United States Patent [19]
Clason et al.

[11] 4,193,980
[45] Mar. 18, 1980

[54] DRY PREPARATION FOR RETICULOCYTE STAINING

[75] Inventors: Stanley E. Clason, Painted Post; John W. Gilliland, Horseheads, both of N.Y.

[73] Assignee: Corning Glass Works, Corning, N.Y.

[21] Appl. No.: 867,199

[22] Filed: Jan. 5, 1978

[51] Int. Cl.$^2$ .................... G01N 33/16; G01N 31/22; G01N 21/60
[52] U.S. Cl. ........................................ 424/3; 252/408; 422/57; 427/4
[58] Field of Search ........................ 23/230 B; 422/57; 427/2, 3, 4; 252/408; 424/3

[56] References Cited

U.S. PATENT DOCUMENTS 4,070,495  1/1978  Berger et al. ...................... 427/4 X

OTHER PUBLICATIONS

Brecher, "New Methylene Blue as a Reticulocyte Stain," Amer. Jour. of Clin. Path., vol. 19, pp. 895–896 (1949).

Robertson, "The Effects of Experimental Plethora on Blood Production," Jour. of Experimental Medicine, vol. 26 pp. 221–237 (1917).

Cunningham, "A Method for the Permanent Staining of Reticulated Red Cells," Archives of Inter. Med., vol. 26, pp. 405–409 (1920).

Vander et al., "Reticulocyte Counts by Means of Fluorescence Microscopy," J. Lab. and Clin. Med. 62, p. 132 (1963).

Marshall et al., "Purified Azure B as a Reticulocyte Stain," J. Clin. Path, 29, pp. 1060–1063 (1976).

Orten, "The Properties and Significance of the Reticulocyte," Yale J. Biol. & Med. 6, pp. 519–539 (1934).

*Primary Examiner*—R. E. Serwin
*Attorney, Agent, or Firm*—William J. Simmons, Jr.; Walter S. Zebrowski

[57] ABSTRACT

A dry stain for reticulocyte staining comprising a mixture of new methylene blue N dye, potassium acetate, and an anti-blood-clotting agent. The stain is prepared in a concentrated aqueous solution, filtered, dispensed volumetrically into tubes, and dried. The correct quantity of dye per tube is determined spectrophotometrically, and the proper ratio of dye to potassium acetate is determined by pH measurements. For staining reticulocytes, whole blood is added to the tube and mixed with the dry stain. Smears are then prepared on slides in a conventional manner for microscopic examination.

11 Claims, 2 Drawing Figures

DRY PREPARATION FOR RETICULOCYTE STAINING

BACKGROUND OF THE INVENTION

This invention relates to a dry stain which can be mixed with whole blood to prepare a microscope slide, and to a method of preparing the stain.

The determination of reticulocyte count as a percentage of total red cells is an extremely useful and important procedure in clinical hematology. A number of techniques have been used for staining blood for such analysis. Most of these techniques involve the use of a liquid stain preparation which is mixed with the blood.

Three techniques for reticulocyte staining are described in *Staining Procedures* (3rd Ed.) edited by George Clark, published for the Biological Stain Commission by the Williams and Wilkens Company, Baltimore, Maryland (pp. 128-130). These techniques are described in the following publications: (1) Brecher, G., New Methylene Blue as a Reticulocyte Stain, American Journal of Clinical Pathology, Vol. 19, pp. 895-896 (1949), (2) Robertson, O. H., The Effects of Experimental Plethora on Blood Production, Journal of Experimental Medicine, Vol. 26, pp. 221-237 (1917), and (3) Cunningham, R. S., A Method for Permanent Staining of Reticulated Red Cells, Archives of Internal Medicine, Vol. 26, pp. 405-409 (1920).

The technique described by Brecher uses a solution of 0.5% new methylene blue N and 1.6% potassium oxalate in water, and this solution is mixed with blood in equal volumes. After 10 to 15 minutes a drop is placed on a slide and a smear is made in a normal manner. The Brecher formula, which is presently the most widely used, has been favored because of the sharper reticulum it produces and because of the consistency of dye purity from batch to batch. One of the problems associated with the Brecher stain is that precipitate forms in it continuously over a long period of time, and therefore, in order to avoid slide artifacts which might interfere with the count, the stain must be filtered each time it is used. If the stain is dried, precipitates form when it is redissolved. Even if the insoluble matter is removed directly prior to drying, more precipitate forms immediately when the stain is dissolved in the blood. This precipitate is probably an insoluble salt of the divalent anions and the new methylene blue N dye.

The Robertson publication describes a wet procedure using brilliant cresyl blue. A saturated aqueous stock solution of the stain is prepared in 0.85% NaCl. The stock is diluted 80-180 times, and 20 volumes of the dilute solution are mixed with one volume of blood. The counts are made of fresh preparations sealed with vasoline to prevent drying. The technique reported by Cunningham also uses brilliant cresyl blue followed by Wright's stain. Using a solution of 0.3% alcoholic brilliant cresyl blue, a drop is dried on a slide. A drop of blood is placed on the stain, mixed, spread and dried. The smear is then counterstained by the normal technique with Wright's stain.

One of the problems with liquid stains is that insoluble granules form continuously in the solution. Since such a precipitate can produce artifacts on the slide which would interfere with the reticulocyte count, the stain must be filtered each time it is used to remove this residue. Following filtration, the stain must be volumetrically dispensed into the blood that is to be analyzed. These are time consuming, inconvenient and messy operations for the modern clinical laboratory.

SUMMARY OF THE INVENTION

It is therefore an object of the present invention to provide a reticulocyte stain that can be prepared in dried form. A further object is to provide such a stain which can be mixed directly with whole blood without forming precipitates which can cause artifact problems. Still another object is to provide a dry stain which can be employed in a reticulocyte staining technique which is cleaner and simpler than techniques employing conventional liquid stains.

Briefly, the stain of the present invention comprises a mixture of new methylene blue N dye, a salt of a strong base and a weak acid of a monovalent anion, and an amount of an anticoagulent effective to prevent the occurrence of blood clotting.

The stain is preferably stored in tubes into which a predetermined volume of blood is to be added. The stain stock solution comprising the dye, salt and anticoagulant is dispensed into the tubes and then dried. As used herein, the word tube means test tube or other suitable container, the shape of which is immaterial.

DESCRIPTION OF THE PREFERRED EMBODIMENTS

The dry stain preparation which is described herein can be mixed directly with blood for reticulocyte staining. The stain is prepared in a disposable stain tube which can be stored under refrigeration until such time that a predetermined volume $V_b$ of blood is added thereto for staining. All volumes referred to herein are measured in ml.

The salt employed in the manufacture of the stain of the present invention increases the pH of the stain into a favorable range around neutrality. A pH value in the range of 5-9 is acceptable, but outside that range the staining is affected, becoming lighter at lower pH values and darker at higher pH values.

Incorporated in the dry stain of the present invention is a dye known in the art as new methylene blue N which is readily available in powdered form. This dye is also known as C. I. No. 52030, which number is taken from the text *Colour Index* edited by F. M. Rowe, 2nd Edition, published by the Society of Dyers and Colourists, Bradford, England and The American Association of Textile Chemists, Lowell, Massachusetts (1956-1958, supplement 1963). To utilize this dye in the method of this invention, a concentrated aqueous solution thereof referred to as the dye stock solution is prepared and filtered or centrifuged to remove insolubles.

A concentrated aqueous solution of a salt of a strong base and a weak acid of a monovalent anion is also prepared. The salt is employed in the manufacture of the stain of the present invention to increase the pH of the stain into a favorable range around neutrality. A pH value in the range of 5-9 is acceptable, but outside that range the staining is affected, stained cells becoming lighter at lower pH values and darker at higher pH values. By strong base is meant a compound such as sodium hydroxide, potassium hydroxide or the like. By a weak acid of a monovalent anion is meant acetic acid, propionic acid, butanoic acid or the like. Preferred salts are sodium acetate and potassium acetate. The two previously prepared aqueous solutions, i.e., the dye and salt solutions, are mixed in such a ratio as to produce the desired pH at the final dilution. This pH value is determined by diluting the contents of a single tube, which aliquot size will be determined hereinbelow, with a volume of deionized water equal to the volume of blood to be added to the stain tube and reading the pH by standard techniques. Although values of pH from 5 to 9 are acceptable, values near 7 are generally preferred. However, other factors such as the effect of the salt on blood coagulation may cause the optimal pH to vary from values near 7.

Figure 1:
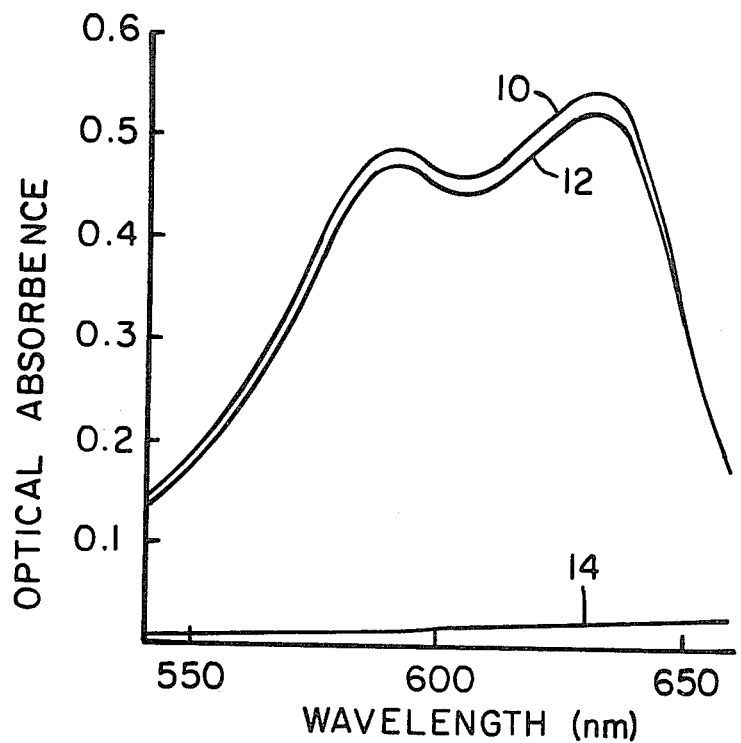
FIG. 1 is a graph illustrating the spectral absorbance of a dye stock solution.

The aliquot size of the mixed solution is determined as follows. A sample volume $V_s$ of the mixed solution of dye and salt is diluted to 500 ml in 0.005 molar, pH 7 phosphate buffer. Using a spectrophotometer, an absorbance spectrum is run from 550 to 650 nm. Since the spectral absorbance is sensitive to temperature, it is necessary to make spectral measurements at a constant temperature, e.g. 22° C. In addition, the solutions may be bleached by excessive exposure to light, so appropriate precautions should be taken. As shown in FIG. 1 an aliquot size corresponding to 50 μl of 10% w/v new methylene blue N dye gives peak absorbance readings in the 0.5 to 1.0 range when the measurement is performed as herein described. Letting D be the average of the absorbances at the two absorbance maxima for a 1 cm light path-length, the aliquot volume $V_a$ is given by $$V_a = K V_b V_s / D \qquad (1)$$

where K is a constant which may be chosen to correspond to the depth of staining desired. For light staining, K is equal to 0.38, and for dark staining, K is equal to 0.75. An intermediate value of K of about 0.53 is preferred. Improved results may be obtained by taking two spectrophotometer readings and averaging the results.

A sufficient amount of an anticoagulant is added to the stock solution to prevent blood clotting or platelet aggregation upon mixture of the solution with whole blood. The exact amount of anticoagulant required will depend somewhat upon the choice of salt in the stock solution. A preferred anticoagulant is ethylene diamine tetracetate anticoagulant (EDTA) which is well known in the art as an anticoagulant for use in the collection of blood samples.

At this point in the process the following control checks can be made on the stain solution. An amount $V_t$ of stain stock solution is mixed with 0.005 M pH 7 phosphate buffer. The volume of said buffer employed is 500 ml for each ml of blood for which the stain tube is designed. Thus. if a volume $V_t$ of stain stock solution sufficient to stain 1.0 ml of blood is to be added to each stain tube, then a volume $V_t$ of stain stock solution is dispensed into 500 ml of said buffer solution. A clean, dry 1 cm diameter cuvette is filled with the resultant solution and placed in a spectrophotometer. The average of the 530 nm and 630 nm peaks is determined in the aforementioned manner. This average optical absorbance should be within the range of 0.38 and 0.75, the preferred value being 0.53.

The pH of the stain stock solution can be determined in the following manner. An amount of distilled water is added to a volume $V_t$ of stain stock solution to form a total volume equal to the volume $V_b$. The measured pH should be substantially equal to the predetermined pH value. Since the volume $V_t$ is usually much smaller than $V_b$, it is often sufficient to add a volume $V_t$ of stain stock solution to a volume $V_b$ of distilled water to make this pH check.

An amount of the resultant mixture suitable for mixing with the predetermined amount $V_b$ of blood is dispensed into a small test tube or similar container referred to herein as a stain tube. The solution is evaporated to dryness in the stain tube by any convenient method; however, excessive heating which could cause degradation of the dye should be avoided. Such evaporation methods as freeze drying and air evaporation may be employed. A small amount of heat may be employed during evaporation. The tubes may then be stored in a sealed container or individually stoppered. When properly sealed, the resultant dry stain may be stored at 2°-6° C. for at least one year.

The dry stain is utilized in the following manner. It has been found to be convenient to employ 1.0 ml samples of blood, and if this volume is employed, the term $V_b$ disappears from equation 1. The blood is added to the tube containing the stain, and the tube is capped and placed on an aliquot mixer for 15 minutes. Smears are then prepared immediately and observed under oil immersion. At the intermediate concentration, wherein the value of K in equation 1 is taken to be 0.53 and the pH value of the mixture of the dye stock solution and the salt solution is in the central region of the preferred range, the red cells appear grey to greenish-grey. The reticulum stands out sharply as dark blue-black strands. With the lower stain concentrations, the red cell staining becomes more reddish, taking on a clay color, while at higher concentrations, their color is blue. The reticulum staining does not appear to change significantly in either case but always remains very dark and distinct. If the staining is too light, it becomes difficult to distinguish cells, whereas dark staining reduces the contrast between the reticulum and background.

A preferred stain, which gives excellent reticulocyte staining, comprises new methylene blue N dye, potassium acetate and EDTA. In accordance with the above described method of forming the dry stain, the dye and salt should be present in relative amounts which are effective, when diluted with a volume $V_b$ pure deionized water, to form a solution, the pH of which is between 5 and 9. The EDTA should be present in an amount that is effective to prevent the occurrence of blood clotting. This preferred composition comprises 30-70 wt.% new methylene blue N, 15-35 wt.% potassium acetate and 15-35 wt.% EDTA, the EDTA preferably being present in an amount equal to the amount of potassium acetate.

Since no precipitation on initial mixing of the salt and dye occurs, it may be advantageous in a manufacturing operation to eliminate the step of mixing the solutions outside the tubes and instead to add aliquots of the two solutions directly to the tubes. By using solutions of the highest concentrations, the volume of liquid to be evaporated will be kept to a minimum.

SPECIFIC EXAMPLE

The lyophilized stain of the present invention is particularly adaptable for storage in small test tubes in amounts necessary to stain a single blood sample, which in the following example is taken to be 1.0 ml whole blood. The following is a typical example of a method of forming such lyophilized stain.

A dye stock solution is prepared by dissolving new methylene blue N (C.I. No. 52030) in distilled water at a concentration of 10%, i.e., 1 gm dye per 10 ml distilled water. Enough reagent for about 20 tubes of lyophilized stain can be obtained from one ml of dye stock. The dye stock solution is then filtered through course filter paper to remove insolubles. A volume of 50 µl of dye stock is diluted in 500 ml 0.005 M pH 7 phosphate buffer. A clean, dry 1 cm diameter cuvette is filled with the resultant solution and placed in a Beckman Model 25 spectrophotometer. The cuvette should not be prerinsed with the solution since it will slightly stain the cuvette, thereby producing an erroneous result. During this process, unnecessary exposure to light should be avoided. As illustrated by curve 10 of FIG. 1, the spectrophotometer is employed to obtain an absorbance spectrum (in optical density units) over the range of 550 nm-650 nm at 22° C. A second 50 µl sample of dye stock is diluted in phosphate buffer as described above and a second absorbance spectrum is obtained on the same graph as illustrated by curve 12 in FIG. 1. The base line or zero absorbance curve is represented by line 14.

the average absorbance D of the two spectra is obtained in the following manner. Curves 10 and 12 have absorbance peaks at 590 nm and 631 nm. The absorbance values of curves 10 and 12 at the 590 nm peak are 0.489 and 0.474, these values being corrected to 0.476 and 0.461 after subtracting the base line value of 0.013 from the actual readings. The average absorbance value of the 590 nm peak is therefore 0.468. Similarly, the average absorbance of the 631 nm peak is obtained by subtracting the base line value of 0.022 from the two absorbance readings of 0.560 and 0.530 to obtain absorbance values of 0.528 and 0.508 for curves 10 and 12, respectively. The average absorbance of the 631 nm peak is therefore 0.518. The average absorbance D of the 590 nm peak and the 631 nm peak is determined to be 0.493.

The volume $V_a$ of dye stock required per tube of lyophilized stain is calculated from equation 1. The intermediate value of 0.53 is employed for the constant K. The sample volume $V_s$ of dye stock employed in the determination of the value of absorbance D was 50 µl; therefore, the value $V_s$ to be substituted into equation 1 is 0.05. For an average absorbance D of 0.493, the aliquot volume is therefore determined to be 0.053 ml to prepare an amount of lyophilized dye to stain 1 ml of blood.

Figure 2:
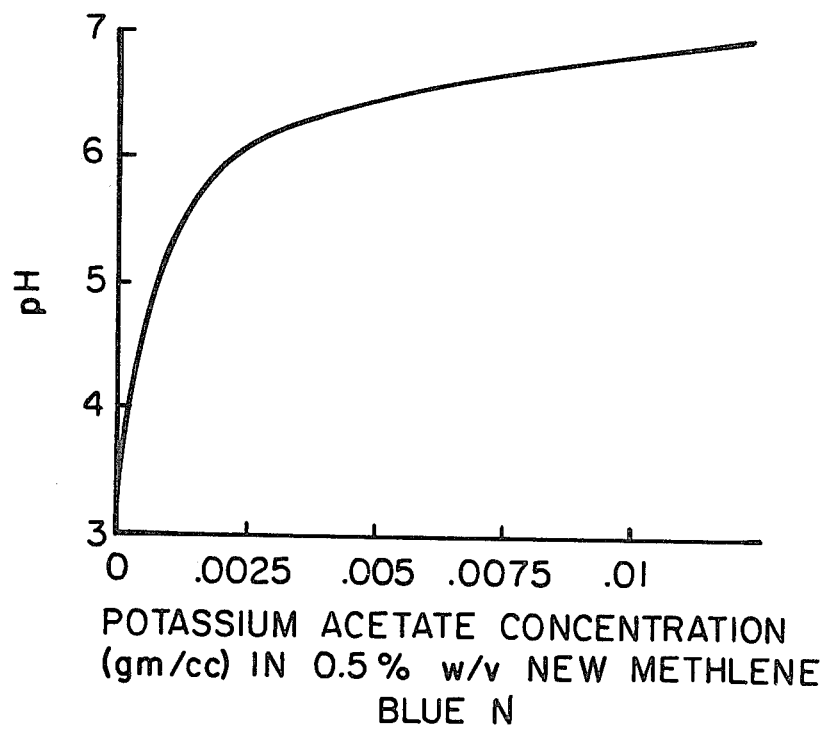
FIG. 2 is a graph wherein pH is plotted as a function of potassium acetate concentration in a solution of new methylene blue N dye.

The stain stock solution, which is the final reagent to be added to the tube just prior to drying, is prepared in the following manner. Potassium acetate is selected as the salt to raise the pH of the stain into a favorable range around neutrality. Since the presence of potassium acetate increases the tendency for blood to coagulate, the lowest amount of potassium acetate was selected to safely prevent the pH level from dropping below the minimum acceptable value of 5.0. Referring to FIG. 2, it can be seen that for concentrations of potassium acetate around 0.0025 grams per cc in a solution of 0.5 grams per 100 cc of new methylene blue N stain, the pH value is about 6 and that the pH value drops sharply at lower concentrations of potassium acetate. The slightly higher pH value of 6.1 was therefore chosen for the pH of the final stain stock solution, thereby necessitating a concentration of potassium acetate of 0.0028 grams per cc of the 0.5% w/v new methylene blue N stain. It is noted that the stated concentration of new methylene blue N stain solution is about that of one aliquot volume $V_a$ diluted to 1.0 cc. The total amount of stain stock solution will therefore require x grams of potassium acetate where x is determined by the equation $$x = 0.0028 \, v_d / V_a \qquad (2)$$

where $V_d$ is the total amount of dye stock solution in ml which has been prepared. Since $V_d$ is 500 ml and $V_a$ has been determined to be 0.053 ml then x can be determined to be 26.42 grams.

As stated previously, the presence of potassium acetate increases the tendency for blood to coagulate; therefore, more EDTA is required than if potassium acetate were not employed. It has been found that an amount of EDTA in the final stain stock solution equivalent to the amount of potassium acetate will provide the necessary anticoagulation effect. Therefore, 26.42 grams of EDTA are employed.

Because of the dispensing equipment employed in the filling of the stain tubes, a minimum amount of the stain stock solution had to be dispensed in each tube to insure accuracy. Therefore, the potassium acetate and EDTA were dissolved in a volume $V_s$ distilled water in ml which was mixed with the dye stock solution to form the final stain stock solution. The volume $V_s$ is determined by the equation $$V_s = V_d \left[ \frac{V_t}{V_a} - 1 \right] \qquad (3)$$

where $V_t$ is the desired volume of stain stock to be dispensed per tube in ml as determined by the dispensing equipment, viz. 0.2 ml. Since $V_d$ is 500 ml and $V_a$ is 0.053 ml, the volume $V_s$ is 1,386.8 ml.

The 26.42 grams of potassium acetate and 26.42 grams of EDTA are added to the 1,386.8 ml of distilled water where these additives dissolve rapidly at room temperature. The resultant solution is mixed with the 500 ml of dye stock solution to form the final reagent to be added to the tubes. Insolubles are removed from this stain stock solution by filtration with coarse filter paper. Prior to dispensing this stain solution, the following control checks are made .

Since 0.2 ml of the stain stock solution is to be dispensed into each stain tube, the same amount of that solution is diluted in 500 ml of 0.005 M pH 7 phosphate buffer in a clean, dry 1 cm cuvette which is placed into a spectrophotometer. Using the method described above in conjunction with FIG. 1, the average absorbance value of the two peaks should be 0.53±0.02 optical density units.

If the optical density is within the prescribed range, the stain stock solution pH is then determined. A single tube volume of 0.2 ml of stain stock solution is diluted in 1 ml of distilled water. The pH value of the resultant solution should be within the range of 6.1±0.3.

If the above quality checks have been met, the stain stock solution is ready for dispensing into the stain tubes. A volume of 0.2 ml of stain stock solution is dispensed into each tube. A precision of ±1% should be maintained during the filling of the tubes. All of the filled tubes are then placed in a refrigerator where the temperature is gradually decreased to −50° C. over a time period of two hours. The refrigerator is then evacuated, and the temperature is then gradually increased to ambient temperature during a two hour time period. The chamber remains evacuated for 2-24 hours to insure removal of the water component of the dispensed stain stock solution. The tubes are then individually corked as soon as possible after they are removed from the lyophilization chamber to avoid the possibility of moisture from the air penetrating the dry stain. The cork must fit well enough to prevent moisture from reaching the dry stain. The tubes can then be stored at 2°-6° C. for at least one year prior to use.

Although the present invention has been described with respect to details of certain embodiments thereof, it is not intended that such details be limitations upon the scope of the invention except insofar as set forth in the following claims.

We claim:

1. A stain tube for staining a volume $V_b$ of blood comprising a tube, and an amount of dry stain in said tube sufficient for staining a volume $V_b$ of blood, said stain comprising a mixture of new methylene blue N dye, a salt of a strong base and a weak acid of a monovalent anion, and an amount of an anticoagulant effective to prevent the occurrence of blood clotting, said dye and said salt being present in relative amounts which are effective, when diluted in a volume $V_b$ of pure deionized water, to form a solution, the pH of which is between 5 and 9.

2. The stain tube of claim 1 wherein said dye is present in an amount in the range of 30-70 weight percent.

3. The stain tube of claim 2 wherein said salt is potassium acetate which is present in an amount within the range of 15-35 weight percent and wherein said anticoagulant is ethylene diamine tetracetate which is present in an amount in the range 15-35 weight percent.

4. The stain tube of claim 1 wherein said salt is a compound of a base selected from the group consisting of potassium hydroxide and sodium hydroxide and an acid selected from the group consisting of acetic acid, propionic acid and butanoic acid.

5. A dry stain for staining blood cells comprising a mixture of new methylene blue N dye, a salt of a strong base and a weak acid of a monovalent anion, and an amount of an anticoagulant effective to prevent the occurrence of blood clotting.

6. The stain of claim 5 wherein said dye is present in an amount in the range of 30-70 weight percent, and wherein said salt is potassium acetate which is present in an amount within the range of 15-35 weight percent and wherein said anticoagulant is ethylene diamine tetracetate which is present in an amount in the range 15-35 weight percent.

7. The stain of claim 5 wherein said salt is a compound of a base selected from the group consisting of potassium hydroxide and sodium hydroxide and an acid selected from the group consisting of acetic acid, propionic acid, and butanoic acid.

8. A method of forming a stain tube containing an amount of dry stain sufficient for staining a volume $V_b$ of blood, said method comprising preparing a volume $V_d$ of a concentrated aqueous solution of new methylene blue N dye, filtering said dye solution, preparing a concentrated aqueous solution of a salt of a strong base and a weak acid of a monovalent anion, mixing said dye solution and said salt solution, adding an anticoagulant to said mixture to form a stain stock solution, dispensing into a tube a volume $V_t$ of said stain stock solution which is sufficient to stain said volume $V_b$ of blood, and drying the stain stock solution in said tube, said dye and said salt being present in said tube in relative amounts which are effective, when the resultant dry stain is diluted in a volume $V_b$ of pure deionized water, to form a solution, the pH of which is between 5 and 9.

9. The method of claim 8 wherein the step of drying comprises lyophilizing the mixture in said tube.

10. The method of claim 9 wherein the step of preparing a concentrated aqueous solution of a salt comprises preparing a concentrated aqueous solution of a compound of a base selected from the group consisting of potassium hydroxide and sodium hydroxide and an acid selected from the group consisting of acetic acid, propionic acid and butanoic acid.

11. The method of claim 8 wherein, prior to the step of dispensing, said volume $V_t$ of said stain stock solution is so constituted that when diluted in 500 ml of 0.005M pH 7 phosphate buffer per ml of blood that is to be added to said tube for staining, a one cm path of the resultant solution will exhibit an average optical absorbance at 500 nm and 630 nm of between 0.38 and 0.75.

* * * * *